United States Patent [19]

Itoh et al.

[11] Patent Number: 4,792,547
[45] Date of Patent: Dec. 20, 1988

[54] PYRAZINE-2-CARBOXAMIDE DERIVATIVES USEFUL IN TREATING ALLERGIC DISEASE

[75] Inventors: Yasuo Itoh; Hideo Kato; Eiichi Koshinaka; Nobuo Ogawa; Kazuya Mitani, all of Fukui, Japan

[73] Assignee: Hokuriku Pharmaceutical Co., Ltd., Katsuyamashi, Japan

[21] Appl. No.: 941,918

[22] Filed: Dec. 15, 1986

[30] Foreign Application Priority Data

Dec. 26, 1985 [JP] Japan .................. 60-291916
Oct. 30, 1986 [JP] Japan .................. 61-256875

[51] Int. Cl.$^4$ .................. A61K 31/55; A61K 31/495; C07D 403/12; C07D 403/14
[52] U.S. Cl. .................. 514/211; 514/212; 514/218; 514/235.8; 514/241; 514/242; 514/252; 514/256; 540/544; 540/554; 540/553; 540/575; 544/96; 544/182; 544/215; 544/333; 544/405
[58] Field of Search .................. 544/405, 120, 357, 96, 544/182, 215, 333; 514/252, 218, 234, 211, 212, 241-242, 256, 235.8; 540/575, 544, 553, 554

[56] References Cited

U.S. PATENT DOCUMENTS

| | | | |
|---|---|---|---|
| 3,966,965 | 6/1976 | Sellstedt et al. | 514/510 |
| 4,044,144 | 8/1977 | Sellstedt et al. | 514/381 |
| 4,112,094 | 9/1978 | Sellstedt et al. | 544/405 X |
| 4,404,214 | 9/1983 | Takeda et al. | 546/276 X |

FOREIGN PATENT DOCUMENTS 005979 1/1987 Japan .................. 544/405

OTHER PUBLICATIONS

Honma et al., J. Med. Chem. 1984, vol. 27, No. 2, pp. 125-128.

Ford et al., J. Med. Chem. 1986, vol. 29, No. 4, pp. 538-549.

Primary Examiner—Donald G. Daus
Assistant Examiner—William A. Teoli, Jr.
Attorney, Agent, or Firm—Gordon W. Hueschen

[57] ABSTRACT

Novel pyrazine derivatives useful for treatment of bronchial asthma, allergic gastorenteric trouble, hay fever urticaria, allertic rhinitis, and allergic conjunctivitis, and pharmaceutical compositions thereof, are disclosed. The compounds have the formula I as follows:

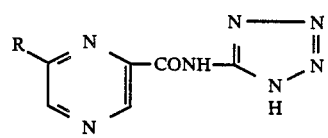

wherein R represents hydrogen or

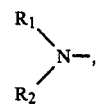

wherein $R_1$ and $R_2$ may be the same or different and each independently represents hydrogen, straight or branched-chain lower-alkyl, or cycloalkyl having three to six carbon atoms inclusive, phenyl which may be substituted with halogen, lower-alkyl, or lower-alkoxy, or wherein $R_1$ and $R_2$ together represent alkylene of four to six carbon atoms, inclusive, optionally interrupted by one or two nitrogen atoms or one oxygen atom and said ring being optionally substituted by straight or branched-chain lower-alkyl having one to six carbon atoms inclusive, hydroxy, or phenyl, and pharmaceutically-acceptable salts thereof.

11 Claims, No Drawings

PYRAZINE-2-CARBOXAMIDE DERIVATIVES USEFUL IN TREATING ALLERGIC DISEASE

The present invention relates to novel derivatives of yyrazine and pharmaceutically-acceptable salts thereof which exhibit an effective anti-allergic activity and can be used for treatment of allergic disease, to a process for the preparation thereof, pharmaceutical compositions of thereof, and a method of treating therewith.

It is already known that disodium cromoglycate(generic name, The Merck Index, 10th Edition, 2580) represented by formula (II)

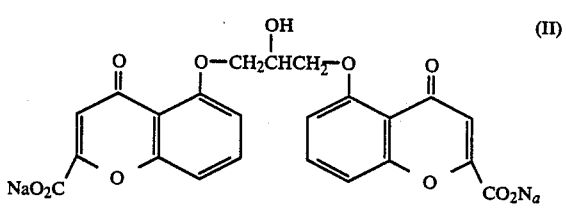

and tranilast(generic name, The Merck Index, 10th Edition, 9392) represented by formula (III)

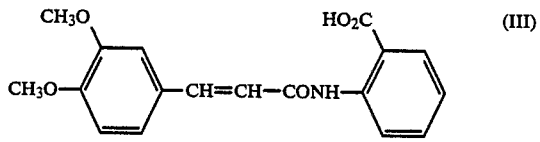

have effective anti-allergic activity and are useful as agents for bronchial asthma and have already have been marketed widely for clinical use.

Furthermore, it is also known that 6-methyl-N-(1H-5-tetrazolyl) pyridine-2-carboxamide (TA-5707F, Jpn, Kokai Tokyyo Koho 82-95984), represented by formula(IV):

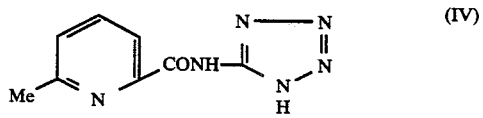

is in some stage of development as an anti-allergic agent.

It has been gradually revealed after the progress of extensive studies in the allergological field that allergic bronchial asthma appears as a result of an antigen-induced allergic reaction of type I upon the entrance of an allergen into the human body, whereupon chemical mediators are released from mast cells. For treating such allergic diseases, an agent which can prevent the release of chemical mediators has been used.

Disodium cromoglycate represented by formula (II) is an agent which has been used for the first time in clinical praxis.

However, it must be administered as only by inhalation in the form of powder or solution, because it can not be used in oral administration, which is disadvantageous because of the use of a special apparatus is required for aspiration and because of a feeling of physical discomfort in the throat.

The second commercial product, tranilast represented by formula (III) is known as an orally active anti-allergic agent for inhibiting the release of chemical mediators.

However the effect of this drug is not adequate. The daily dosage for effective treatment is about 300 mg and this is accompained by side effects in the digestive system, such as nausea, abdominal pain, and gastric discomfort.

As explained above the effect of the known drugs of this field was not yet sufficient, so that it was necessary to find and develop another drug for this purpose.

As a result of extensive investigation on new drugs, which can inhibit the release of chemical mediators, it has been found that, after study of the compounds having a tetrazole group in the structure, the pyrazine derivatives of this application possess an effective antiallergic activity and thus the present invention has been accomplished.

The invention of this application relates to derivatives of pyrazine represented by the general formula

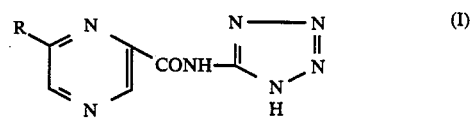

wherein R represents hydrogen atom or

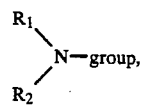

wherein $R_1$ and $R_2$, which may be the same or different, represent hydrogen atom, straight or branched-chain lower alkyl group or cycloalkyl group having 3 to 6 carbon atoms, phenyl group, which may be substituted with halogen, lower alkyl group or lower alkoxyl group, or 5 to 7 membered-ring together with the neighborous nitrogen atom, which may have oxygen atom nitrogen atom or sulfur atom as ring-member and may be substituted with substituent, and pharamaceutically-acceptable salts thereof.

As examples of straight or branched-chain lower alkyl groups, $R_1$ and $R_2$ of the general formula (I) are methyl-, ethyl-, propyl-, isopropyl-, butyl-, isobutyl-, sec-butyl-, tert-butyl-, hexyl-, and dodecyl-group.

Examples of cycloalkyl group having 3 to 6 carbon atoms ar cyclopropyl-, cyclobutyl-, cyclopentyl-, and cyclohexy-group.

The examples of substituent of the phenyl group are halogen such as fluorine, chlorine, bromine, iodine atom, lower alkyl group such as methyl-, ethyl-, propyl-, isopropyl-, butyl-, isobutyl-group etc. and lower alkoxyl group such as methoxy-, ethoxy-, propoxy-group etc. Examples of 5 to 7membered-ring, which together with the neighborous nitrogen atom, are pyrrolidinyl-, piperidinyl-, methylpiperidinyl-, hydroxypiperidinyl-, hexahydroazepinyl-, piperazinyl-, 4-methylpiperazinyl-, 4-ethylpiperazinyl-, 4-acetylpiperazinyl-, 4-phenylpiperazinyl-, morpholinyl-, thiomorpholinyl-, homopiperazinyl-, 4-methylhomopiperazinylgroup etc.

Pharmacologically-acceptable salts of the compound having the said general formula (I) are acid additional salt or alkali additional salts. The former includes mineral acid salts such as hydrochloride, sulfate, nitrate, hydrobromide, hydroiodide, phosphate, etc.; or organic acid salts such as acetate, maleate, fumarate, citrate, or tartarate, etc. The latter includes inorganic alkali salts such as sodium, potassium, calcium or ammonium salt, etc.; or organic base salts such as ethanol amine salt, N,N-dialkyl ethanol amine salt, and tris (hydroxymethyl) aminomethane etc.; or basic amino acid salts such as lysine, arginine, and histidine salt etc.

In the first method, the compound having the said formula (I) is obtained by reacting a 6-halogenopyrazine derivative having the following general formula(V),

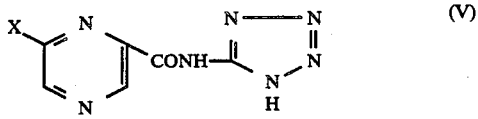

wherein X is a halogen atom, with an amine derivative represented by the following general formula (VI),

wherein $R_1$ and $R_2$ each has the same meaning as that described above, in the presence or absence of a solvent.

The solvent used in this reaction can be any kind so far as it does not inhibit the reaction. The example of solvent is water, alcohols such as methanol, ethanol, propanol, buaanol; ethers such as ethyleneglycol dimethyl ether (monoglyme), diethyleneglycol dimethyl ether (diglyme), triethyleneglycol dimethyl ether (triglyme); aprotic polar solvents such as dimethylformamide, dimethylsulfoxide or hexamethylphosphoric triamide; aromatic hydrocarbons such as benzene or toluene; or organic bases such as pyridine, picoline, lutidine, collidine or trietylamine. Preferably can be used ethanol, benzene, dimethysufoxide.

The reaction can be carried out under normal or elevated pressure and at a temperature from room temperature to 200° C., prefeable from 80° C. to 110° C.

The starting material of this method, represented by the general formula (V) can be prepared by following method.

The compound having the said formula (V) is obtained by reacting pyrazine carboxylic acid derivatives of the following general formula (VII),

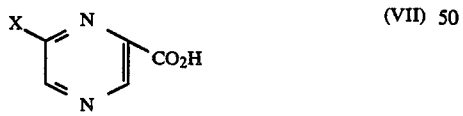

wherein X has the same meaning as that described above, with 5-amino-1H-tetrazole represented by the following formula (VIII).

According to the second method, the inventive compound represented by the general formula (I) is prepared from derivatives of pyrazine-2-carboxylic acid represented by the following general formula (IX),

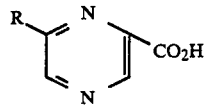

wherein R has the same meaning as that described above, after conversion of the carboxyl group to a functional group, for example acid chloride, acid anhyrride, mixed acid anhydride, with a 5-amino-1H-tetrazole(-VIII) in the presence or absence of a solvent.

The base used in the process of this invention is, for example, pyridine, picoline, lutidine, collidine, N-methylpiperidine, N-methylpyrrolidine, N-methylmorpholine, triethylamine, potassium carbonate, sodium carbonate etc. Preferably can be used the triethylamine.

The inert organic solvent used in this reaction can be any kind so far as it does not inhibit the reaction. The examples are ether, benzene, tetrahydrofuran, dioxane, chloroform, methylene chloride, dimethylsulfoxide, N,N-dimethylformamide etc., preferably can be used tetrahydrofuran.

The reaction can be carried out at a temperature from −10° C. to boiling point, preferably at a temperature from room temperature to the boiling point of the solvent used.

The derivatives of pyrazine-2-carboxylic acid represented by formula (IX), which can be used as a starting material for the process of this invention are known, in literatures, Dissertationes pharmaeutiae pharmacologicae, 24, p.577, (1972).

The thus prepared derivatives of pyrazine represented by formula (I) and pharmaceutically-acceptable salts thereof exhibit an effective anti-allergic activity, expectorant activity, and can be used extremely favourably as medicine for treating of bronchial asthma, food allergy, hay fever, alergic urticaria, allergic rhinitis, allergic conjunctivitis and can be used topically or by oral administration.

As an example to show the excellent effect of the present compounds, its inhibitory effect of histamine release is shown below in Table 1 an the acute toxicity values in Table 2.

1. Inhibitory effect of histamine release

The inhibitory effect of histamine release was examined with the under method, while using disodium cromoglycate(II), tranilast (III), and TA-5707F(IV)as reference drugs.

Mixed peritoneal cells obtained from male Wistar rats weighing 350–400 g were sensitized by incubating for 2 hr at 37° C. with anti-DNP-As rat serum (produced according to the method of Tada and Okumura [Tada, T. and Okmura, K.: J. Immunology, 106,1002 (1971)]. The cell suspension containing about $1 \times 10^5$ mast cells/ml was prepared in Hepes Tyrode buffer containing heparin (10 unit/ml) and BSA (0.3%). This suspension was divided into 0.8 ml aliquots in separate polyethylene tubes. Aliquots of the cell suspension were preincubated at 37° C. for 10 min, and then 0.1 ml of the test compounds were added in various concentrations. After incubation at 37° C. for 1 min, 0.1 ml of DNP-As solution (50μg/ml) were added, followed by incubation at 37° C. for 2 min. The reactio was terminated by adding 2 ml of the cold buffer. The supernatants were separated by centrifugation, the cell pellets were resuspended in 3 ml buffer and placed for 3 min in the heating block (100° C.) to release the residual histamine into cells. The histamine was quantitated using the spedrofluorometric technique of modified Shore's method. The IC 50 was obtained from the dose-response curve.

Results are shown in Table 1.

TABLE 1

| Inhibitory effect on histamine release | |
|---|---|
| Test compound | $IC_{50}$ (M) value |
| Example 2 | $2.5 \times 10^{-9}$ |
| Example 3 | $2.0 \times 10^{-9}$ |
| Example 4 | $1.7 \times 10^{-8}$ |
| Example 5 | $5.0 \times 10^{-9}$ |
| Example 6 | $4.7 \times 10^{-10}$ |
| Example 7 | $1.5 \times 10^{-8}$ |
| Example 8 (free) | $1.2 \times 10^{-9}$ |
| Example 9 | $5.6 \times 10^{-9}$ |
| Example 14 | $3.6 \times 10^{-8}$ |
| Example 15 | $3.6 \times 10^{-8}$ |
| Example 16 | $6.2 \times 10^{-11}$ |
| disodium cromoglycate (II) | $1.9 \times 10^{-7}$ |
| tranilast (III) | $2.4 \times 10^{-5}$ |
| TA-5707F (IV) | $4.6 \times 10^{-8}$ |

2. Acute toxicity test

Male ICR mice 5 weeks old were used as 5 animals at a group. The compounds were administered orally at each dosage.

Results are shown in Table 2.

TABLE 2

| Acute Toxicity | |
|---|---|
| test compound | $LD_{50}$ (mg/kg) |
| Example 8 (free) | >2000 |
| Example 8 (sodium salt) | >2000 |

A compound of the present invention represented by general formula (I) can be administrated per os, e.g., in the form of pills or tablets, in which it may be present together with any of the usual pharmaceutical carriers, conventionally by compounding a compound of this invention together with a customary carrier or adjuvant, such as talc, magnesium stearate, starch, lactose, gelatin, any of numerous gums, and the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, terra alba, dicalcium acacia, or the like. Representative liquid carriers are peanut oil, sesame oil, olive oil, water, or the like. The active agents of this invention can be conveniently administered in such compositions containing active ingredient so as to eventually be within the dosage range illustrated hereafter. Thus, a wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion, whereas, for parenteral administration, the composition may be in the form of a sterile solution.

The method of using the compounds of this invention comprises internally or externally administering a compound of this invention, preferably orally or parenterally and preferably admixed with the pharmaceutical carrier, for example, in the form of any of the above compositions, or filled into a capsule, to aleviate conditions to be treated and symptoms thereof in a living animal body. Illustratively, it may be used in an amount of about 1 to about 1000 mg per day (divided into three parts), preferably in amount of 1 to 100 mg per day (divided into three parts) for an oral dose, while parenteral dosages are usually less and ordinarily about one-half of the oral dose. The unit dose is preferably given a suitable number of times daily, typically three times. For dropping lotion in the dyes and nose it may be used in an amount of about 0.1 to 100 mg preferably 1 to 50 mg at a time.

The unit dose may vary depending upon the number of times given. Naturally, a suitable clinical dose must be adjusted in accordance with the condition, age, and weight of the patient, and it goes without saying that the enhanced activities of the compounds of the invention, together with their reduced side effects, also make them suitable for wide variations, and this invention therefore should not be limited by the exact ranges stated. The exact dosage, both unit dosage and daily dosage, will of course have to be determined according to established medical principles.

The following examples are given by way of illustration only and are not to be construed as limitations of this invention, many variations of which are possible without departing from the scope and spirit thereof.

Reference: 6-Chloro-N-(1H-5-tetrazolyl)pyrazine-2-carboxamide

To a suspension of 1.59 g of 6-chloropyrazine-2-carboxylic acid in 30 ml of tetrahydrofuran, 1.54 ml of triethylamine and 1.36 ml of pivaloyl chloride were added dropwise successively at 0° C. under stirring. After stirring for 1 hour at 0° C., 0.94 g of 5-amino-1H-tetrazol was added to the mixture, and the reaction mixture was refluxed for 18 hours. After cooling, 50 ml of water was added to the reaction mixture. The precipitate was collected by filtration, and recrystalized from a mixture of dimethylsulfoxide and methanol affording 0.78 g of the desired compound as pale red crystals, m.p. 261°–26° C. (decomp.).

Analysis: $C_6H_4ClN_7O$: Calcd. %: C, 31.94; H, 1.79; N, 43.46. Found %: C, 32.03; H, 1.70; N, 43.68.

EXAMPLE 1

N-(1H-5-Tetrazolyl)pyrazine-2-carboxamide

To a suspension of 1.50 g of pyrazine-2-carboxylic acid in 50 ml of tetrahydrofuran, 1.85 ml of triethylamine and 1.27 ml of ethyl chlorocarbonate were added dropwise successively at 0° C. under stirring. After stirring for 30 minutes at 0° C., 1.35 g of 5-amino-1H-tetrazole was added to the mixture, and the reaction mixture was stirred for 28.5 hours at room temperature. The precipitate was collected by filtration, and washed with dilute hydrochloric acid affording 2.05 g as colorless crystals, which was recrystalized from dimethylsulfoxide giving colorless crystals, m.p. 291°–296 ° C. (decomp.).

Analysis: $C_6H_5N_7O$: Calcd. %: C, 37.70; H, 2.64; N, 51.29. Found %: C, 37.43; H, 2.97; N, 51.74.

EXAMPLE 2

6-(Methylamino)-N-(1H-5-tetrazolyl)pyrazine-2-carboxamide

To a suspension of 2.26 g of 6-chloro-N-(1H-5-tetrazolyl)pyrazine-2-carboxamide in 30 ml of ethanol, 6.50 ml of 30%-methylamine ethanol solution was added, and the mixture was heated for 24 hours at 80°–90° C. in a sealed tube. The reaction mixture was adjusted with ethanolic hydrogen chloride to pH 3. The precipitate was collected by filtration, and recrystalized from a mixture of dimethylsulfoxide and methanol affording 1.57 g of the desired compound as pale yellow needles, m.p. 260° C. (decomp.).

Analysis:$C_7H_8N_8O$: Calcd. %: C, 38.18; H, 3.66; N, 50.89.

Found %: C, 38.16; H, 3.85; N, 51.14.

EXAMPLE 3

6-(Ethylamino)-N-(1H-5-tetrazolyl)pyrazine-2-carboxamide

To a suspension of 2.26 g of 6-chloro-N-(1H-5-tetrazolyl)pyrazine-2-carboxamide in 30 ml of ethanol, 4.05 ml of 70%-ethylamine aqueous solution was added, and the mixture was heated for 24 hours at 80°–90° C. in a sealed tube. The reaction mixture was adjusted with ethanolic hydrogen chloride to pH 3. The precipitate was collected by filtration, and recrystalized from a mixture of dimethylsulfoxide and methanol affording 1.66 g of the desired compound as pale yellow needles, m.p. 272°–273.5° C. (decomp.).

Analysis:$C_8H_{10}N_8O$: Calcd. %: C,41.02; H,4.30; N,47.84. Found %: C,40.95; H,4.45; N,47.99.

EXAMPLE 4

6-(n-Propylamino)-N-(1H-5-tetrazolyl)pyrazine-2-carboxamide

To a suspension of 1.13 g of 6-choloro-N-(1H-5-tetrazolyl)pyrazine-2-carboxamide in 20 ml of ethanol, 2.06 ml of n-propylamine was added, and the mixture was heated for 24 hours at 80°–90° C. in a sealed tube. The reaction mixture was adjusted with ethanolic hydrogen chloride to pH 3. The precipitate was collected by filtration, and recrystalized from a mixture of dimethylsulfoxide and methanol affording 0.91 g of the desired compound as pale yellow needles, m.p. 278°–279.5° C. (decomp.).

Analysis:$C_9H_{12}N_8O$: Calcd. %: C,43.54; H,4.87; N,45.14. Found %: C,43.42; H,5.23; N,44.91.

EXAMPLE 5

6-(Isopropylamino)-N-(1H-5-tetrazolyl)pyrazine-2-carboxamide

To a suspension of 2.26 g of 6-chloro-N-(1H-5-tetrazolyl)pyrazine-2-carboxamide in 30 ml of ethanol, 4.26 ml of isopropylamine was added, and the mixture was heated for 44 hours at 80°–90° C. in a sealed tube. The reaction mixture was adjusted with ethanolic hydrogen chloride to pH 3. The precipitate was collected by filtration, and recrystalized from a mixture of dimethylsulfoxide and methanol affording 1.36 g of the desired compound as pale yellow needles, m.p. 272°–274° C. (decomp.).

Analysis:$C_9H_{12}N_8O$: Calcd. %: C,43.54; H,4.87; N,45.14. Found %: C,43.51; H,5.00; N,45.49.

EXAMPLE 6

6-(Dimethylamino)-N-(1H-5-tetrazolyl)pyrazine-2-carboxamide (a) To a suspension of 30 g of 6-chloro-N-(1H-5-tetrazolyl)pyrazine-2-carboxamide in 260 ml of ethanol, 60 ml of 50%-dimethylamine aqueous solution was added, and the mixture was heated for 9 hours at 80°–90° C. in an autoclave. The reaction mixture was adjusted with concentrated hydrochloric acid to pH 2. The precipitate was collceted by filtration, and recrystalized from a mixture of dimethylsulfoxide and methanol affording 23.1 g of the desired compound as yellow needles, m.p. 267°–269° C. (decomp.).

Analysis:$C_8H_{10}N_8O$: Calcd. %: C,41.02; H,4.30; N,47.84. Found %: C,40.95; H,4.63; N,47.83.

(b) To a suspension of 0.58 g of 6-(dimethylamino)-pyrazine-2-carboxylic acid in 10 ml of tetrahydrofuran, 0.53 ml of triethylamine and 0.47 ml of pivaloyl chloride were added dropwise successively at 0° C. under stirring. After stirring for 1 hour at 0° C., 0.33 g of 5-amino-1H-tetrazole was added to the mixture, and the reaction mixture was stirred for 1 hour at room temperature, and then refluxed for 6 hours. After cooling, 70 ml of water was added to the reaction mixture. The precipitate was collected by filtration, and recrystalized from a mixture of dimethylsulfoxide and methanol affording 0.36 g of the desired compound as yellow needles. The obtained crystal was consistent with that of (a).

EXAMPLE 7

6-(Diethylamino)-N-(1H-5-tetrazolyl)pyrazine-2-carboxamide

To a suspension of 1.13 g of 6-chloro-N-(1H-5-tetrazolyl)pyrazine-2-carboxamide in 20 ml of benzene, 20 ml of diethylamine was added, and the mixture was heated for 24 hours at 80°–90° C. in a sealed tube. The reaction mixture was evaporated. Water was added to the residue, and then the aqueous solutron was adjusted with dilute hydrochloric acid to pH 3. The precipitate was collected by filtration, and recrystalized from a mixture of dimethylsulfoxide and methanol affording 0.75 g of the desired compound as yellow plates, m.p. 217°–218° C.

Analysis:$C_{10}H_{14}N_8O$: Calcd. %: C,45.80; H,5.38; N,42.72. Found %: C,45.57; H,5.67; N,42.84.

EXAMPLE 8

6-(1-Pyrrolidinyl)-N-(1H-5-tetrazolyl)pyrazine-2-carboxamide (a) To a suspension of 200 g of 6-chloro-N-(1H-5-tetrazolyl)pyrazine-2-carboxamide in 1800 ml of ethanol, 220 ml of pyrrolidine was added, and the mixture was refluxed for 22 hours. The reaction mixture was adjusted with concentrated hydrochloric acid to pH 3. The precipitate was collected by filtration, and recrystalized from a mixture of dimethylsulfoxide and methanol affording 193 g of the desired compound as yellow needles, m.p. 273°–275° C. (decomp.).

Analysis:$C_{10}H_{12}N_8O$: Calcd. %: C,46.15; H,4.65; N,43.05. Found %: C,46.14; H,4.91; N,43.43.

(b) To a suspension of 2.90 g of 6-(1-pyrrolidinyl)pyrazine-2-carboxylic acid in 45 ml of tetrahydrofuran, 2.30 ml of triethylamine and 2.00 ml of pivaloyl chloride were added dropwise successively at 0° C. under stirring. After stirring for 1 hour at 0° C., 1.40 g of 5-amino-1H-tetrazole was added to the mixture, and the reaction mixture was stirred for 1 hour at room temperature, and then refluxed for 12 hours, The reaction mixture was evaporated, and water was added to the residue. The precipitate was collected by filtration, and recrystalized from dimethylsulfoxide affording 1.63 g of the desired compound as yellow needles. The obtained crystal was consistent with that of (a)

6-(1-Pyrrolidinyl)-N-(1H-5-tetrazolyl)pyrazine-2-carboxam ide sodium salt.

21.6 g of 6-(1-pyrrolidinyl)-N-(1H-5-tetrazolyl) pyrazine-2-carboxamide was dissolved in 110 ml of water and 29.8 ml of 10%-sodium hydroxide aqueous solution. 465 Ml of ethanol was added to the aqueous solution, and the mixture was cooled for 1 hour at 0 °C. The precipitate was collected by filtration, and recrystalized from aqueous ethanol affording 17.6 g of the sodium salt as yellow columns, m.p. 300>° C.

Analysis: $C_{10}H_{11}N_8O$ Na: Calcd. %: C,42.56; H,3.93; N,39.70. Found %: C,42.44; H,4.16; N,39.89.

EXAMPLE 9

6-(1-Piperidinyl)-N-(1H-5-tetrazolyl)pyrazine-2-carboxamide (a) To a suspension of 30 g of 6-chloro-N-(1H-5-tetrazolyl)pyrazine-2-carboxamide in 270 ml of ethanol, 39.4 ml of piperidine was added, and the mixture was refluxed for 15 hours. The reaction mixture was adjusted with ethanolic hydrogen chloride to pH 3. The precipitate was collected by filtration, and recrystalized from a mixture of dimethylsulfoxide and methanol affording 26.4 g of the desired compound as yellow columns, m.p. 247°–250 °C. (decomp.).

Analysis: $C_{11}H_{14}N_8O$: Calcd. %: C,48.17; H,5.14; N,40.85. Found %: C,48.12; H,5.38; N,40.93.

(b) To a suspension fo 1.28 g of 6-(1-piperidinyl) pyrazine-2-carboxylic acid in 18 ml of tetrahydrofuran, 0.95 ml of triethylamine and 0.84 ml of pivaloyl chloride were added dropwise successively at 0 °C. under stirring. After stirring for 1 hour at 0 °C., 0.58 g of 5-amino-1H-tetrazole was added to the mixture, and the reaction mixture was stirred for 30 minutes at room temperature, and then refluxed for 12 hours. The reaction mixture was evaporated, and water was added to the residue. The precipitate was collected by filtration, and recrystalized from a mixture of dimethylsulfoxide and methanol affording 0.55 g of the desired compound as yellow columns. The obtained crystal was consistent with that of (a).

EXAMPLE 10

6-(3-Methyl-1-piperidinyl)-N-(1H-5-tetrazolyl)pyrazine-2-carboxamide

To a suspension of 1.13 g of 6-chloro-N-(1H-5-tetrazolyl)pyrazine-2-carboxamide in 20 ml of benzene, 2.94 ml of 3-methylpiperidine was added, and the mixture was refluxed for 6 hours. The reation mixture was evaporated, ethanol was added to the residue, and then the ethanol solution was adjusted with ethanolic hydrogen chloride to pH 3. The precipitate was collected by filtration, and recrystalized from a mixture of dimethylsulfoxide and methanol affording 0.81 g of the desired compound as pale yellow columns, m.p. 236.5°–238.5 °C.

Analysis: $C_{12}H_{16}N_8O$: Calcd. %; C,49.99; H,5.59; N,38.87. Found %; C,49.77; H,5.77; N,38.79.

EXAMPLE 11

6-(4-Methyl-1-piperidinyl)-N-(1H-5-tetrazolyl)pyrazine-2-carboxamide

To a suspension of 1.13 g of 6-chloro-N-(1H-5-tetrazolyl)pyrazine-2-carboxamide in 20 ml of benzene, 2.96 ml of 4-methylpiperidine was added, and the mixture was refluxed for 5 hours. The reaction mixture was evaporated, ethanol was added to the residue, and then the ethanol solution was adjusted with ethanolic hydrogen chloride to pH 3. The precipitate was collected by filtration, and recrystalized from a mixture of dimethylsulfoxide and methanol affording 1.02 g of the desired compound as yellow columns, m.p. 246.5°–248.5° C. (decomp.).

Analysis: $C_{12}H_{16}N_8O$: Calcd. %; C,49.99; H,5.59; N,38.87. Found %; C,49.72; H,5.94; N,38.91.

EXAMPLE 12

6-(3-Hydroxy-1-piperidinyl)-N-(1H-5-tetrazolyl)pyrazine-2-carboxamide

To a suspension of 1.13 g of 6-chloro-N-(1H-5-tetrazolyl)pyrazine-2-carboxamide in 20 ml of ethanol, 1.52 g of 3-hydroxypiperidine was added, and the mixture was refluxed for 6 hours. The reaction mixture was adjusted with ethanolic hydrogen chloride to pH 3. The precipitate was collected by filtration, and recrystalized from a mixture of dimethylsulfoxide and methanol affording 0.93 g of the desired compound as yellow crystals, m.p. 257°–259° C. (decomp.).

Analysis: $C_{11}H_{14}N_8O_2$: Calcd. %: C,45.51; H,4.86; N,38.60. Found %: C,45.41; H,5.16; N,38.42.

EXAMPLE 13

6-(4-Hydroxy-1-piperidinyl)-N-(1H-5-tetrazolyl-)pyrazine-2-carboxamide

To a suspension of 1.13 g of 6-chloro-N-(1H-5-tetrazolyl)pyrazine-2-carboxamide in 20 ml of ethanol, 1.52 g of 4-hydroxypiperidine was added, and the mixture was refluxed for 6 hours. The reaction mixture was adjusted with ethanolic hydrogen chloride to pH 3. The precipitate was collected by filtration, and recrystalized from a mixture of dimethylsulfoxide and methanol affording 1.00 g of the desired compound as pale yellow crystals, m.p. 259.5°–261° C. (decomp.).

Analysis: $C_{11}H_{14}N_8O_2$: Calcd. %: C,45.51; H,4.86; N,38.60. Found %: C,45.35; H,5.15; N,38.57.

EXAMPLE 14

6-(4-Morpholinyl)-N-(1H-5-tetrazolyl)pyrazine-2-carboxamide (a) To a suspension of 2.26 g of 6-chloro-N-(1H-5-tetrazolyl)pyrazine-2-carboxamide in 30 ml of ethanol, 4.36 ml of morpholine was added, and the mixture was refluxed for 18 hours. The reaction mixture was adjusted with concentrated hydrochloric acid to pH 2. The precipitate was collected by filtration, and recrystalized from a mixture of dimethylsulfoxide and methanol affording 2.06 g of the desired compound as yellow needles, m.p. 276°–278° C. (decomp.).

Analysis: $C_{10}H_{12}N_8O_2$: Calcd. %: C,43.48; H,4.38; N,40.56. Found %: C,43.47; H,4.56; N,40.70.

(b) To a suspension of 2.50 g of 6-(4-morpholinyl) pyrazine-2-carboxylic acid in 50 ml of tetrahydrofuran, 3.60 ml of triethylamine and 1.60 ml of pivaloyl chloride were added dropwise successively at 0° C. under stirring. After stirring for 1 hour at 0° C., 1.12 g of 5-amino-1H-tetrazole was added to the mixture, and the reaction mixture was stirred for 1 hour at room temperature, and then refluxed for 12 hours. The reaction mixture was evaporated, and water was added to the residue. The precipitate was collected by filtration, and recrystalized from a mixture of dimethylsulfoxide and methanol affording 1.74 g of the desired compound as yellow needles. The obtained crystal was consistent with that of (a).

EXAMPLE 15

6-(4-Methyl-1-piperazinyl)-N-(1H-5-tetrazolyl)pyrazine-2-carboxamide hydrochloride hydrate To a suspension of 2.26 of 6-chloro-N-(1H-5-tetrazolyl) pyrazine-2-carboxamide in 30 ml of ethanol, 5.55 ml of N-methylpiperazine was added, and the mixture was refluxed for 6 hours. The reaction mixture was adjusted with ethanolic hydrogen chloride to pH 1. The precipitate was collected by filtration, and recrystalized from a mixture of dimethylsulfoxide and methanol affording 2.27 g of the desired compound as pale yellow crystals, m.p. 246°–250 ° C. (decomp.).

Analysis: $C_{11}H_{15}N_9O \cdot HCl \cdot H_2O$: Calcd. %: C,38.43; H,5.28; N,36.67. Found %: C,38.22; H,5.15; N,36.71.

EXAMPLE 16

6-(Phenylamino)-N-(1H-5-tetrazolyl)pyrazine-2-carboxamide

To a suspension of 1.13 g of 6-chloro-N-(1H-5-tetrazolyl)pyrazine-2-carboxamide in 5 ml of dimethylsulfoxide, 4.55 ml of aniline was added, and the mixture was heated for 17 hours at 80°–90 ° C. Water and 10%-sodium hydroxide aqueous solution were added to the reaction mixture, and the aqueous alkaline solution was washed with chloroform. The aqueous layer was filtered, and the filtrate was adjusted with 10%-hydrochloric acid to pH 3. The precipitate was collected by filtration, and recrystalized from a mixture of dimethylsulfoxide and ethanol affording 0.80 g of the desired compound as yellow needles, m.p. 290°–293.5° C. (decomp.).

Analysis: $C_{12}H_{10}N_8O$: Calcd. %: C,51.06; H,3.57; N,39.70. Found %: C,51.16; H,3.86; N,39.68.

EXAMPLE 17

6-[(3-Cholorophenyl)amino]-N-(1H-5-tetrazolyl)pyrazine-2-carboxamide

To a suspension of 1.13 g of 6-chloro-N-(1H-5-tetrazolyl)pyrazine-2-carboxamide in 10 ml of dimethylsulfoxide, 5.39 ml of m-chloroaniline was added, and the mixture was heated for 76 hours at 80°–90 ° C. Water and 10%-sodium hydroxide aqueous solution were added to the reaction mixture, and the aqueous alkaline solution was washed with chloroform. Aqueous layer was filtered, and the filtrate was adjusted with 10%-hydrochloric acid to pH 3. The precipitate was collected by filtration, and recrystalized from a mixture of dimethylformamide and ethanol affording 0.34 g of the desired compound as yellow crystals m.p. 281°–289 ° C. (decomp.).

Analysis: $C_{12}H_9ClN_8O$: Calc..%: C,45.51; H,2.86; N,35.38. Found %: C,45.26; H,3.10; N,35.03.

EXAMPLE 18

6-[(2-Methylphenyl)amino]-N-(1H-5-tetrazolyl)-pyrazine-2-carboxamide

To a suspension of 1.13 g of 6-chloro-N-(1H-5-tetrazolyl)pyrazine-2-carboxamide in 5 ml of dimethylsulfoxide, 5.35 ml of o-toluidine was added, and the mixture was heated for 24 hours at 100°–110 ° C. Water and 10%-sodium hydroxide aqueous solution were added to the reaction mixture, and the aqueous alkaline solution was washed with chloroform. Aqueous layer was filtered and the filtrate was adjusted with 10%-hydrochloric acid to pH 3. The precipitate was collected by filtration, and recrystalized from a mixture of dimethylformamide and ethanol affording 0.19 g of the desired compound as dark yellow crystals, m.p. 277°–282° C. (decomp.).

Analysis: $C_{13}H_{12}N_8O$: Calcd. %: C,52.70; H,4.08; N,37.82. Found %: C,52.85; H,4.28; N,38.18.

EXAMPLE 19

6-[(3-Methylphenyl)amino]-N-(1H-5-tetrazolyl)-pyrazine-2-carboxamide

To a suspension of 1.13 g of 6-chloro-N-(1H-5-tetrzolyl) pyrazine-2-carboxamide in 10 ml of dimethylsulfoxide, 5.40 ml of m-toluidine was added, and the mixture was heated for 22 hours at 100°–110° C. Water and 10%-sodium hydroxide aqueous solution was added to the reaction mixture, and the aqueous alkaline solution was washed with chloroform. Aqueous layer was filtered, and the filtrate was adjusted with 10%-hydrochloric acid to pH 3. The precipitate was collected by filtration, and recrystalized from a mixture of dimethylsulfoxide and methanol affording 0.68 g of the desired compound as yellow needles, m.p. 278.5°–284 ° C. (decomp.).

Analysis: $C_{13}H_{12}N_8O$: Calcd.%: C, 52.70; H,43.08; N,37.82. Found %: C,52.56; H,4.17; N,38.18.

EXAMPLE 20

6-[(4-Methylphenyl)amino]-N-(1H-5-tetrazolyl)-pyrazine-2-carboxamide

To a suspension of 1.13 g of 6-chloro-N-(1H-5-tetrazolyl)pyrazine-2-carboxamide in 15 ml of dimethylsulfoxide, 5.36 g of p-toluidine was added, and the mixture was heated for 18 hours at 80°–90 ° C., and heated for 6 hours at 100°–110 ° C. Water and 10%-sodium hydroxide aqueous solution was added to the reaction mixture, and the aqueous alkaline solution was washed with chloroform. Aqueous layer was filtered, and the filtrate was adjusted with 10%-hydrochloric acid to pH 3. The precipitate was collected by filtration, and recrystalized from a mixture of dimethylsulfoxide and methanol affording 0.93 g of the desired compound as yellow needles, m.p. 289.5°–294 ° C. (decomp.).

Analysis: $C_{13}H_{12}N_8O$: Calc. %: C,52.70; H,4.08; N,37.82. Found %: C,52.83; H,4.29; N,38.08.

EXAMPLE 21

6-[(4-Methoxyphenyl)amino]-N-(1H-5-tetrazoly)pyrazine-2-carboxamide

To a suspension of 1.13 g of 6-chloro-(1H-5-tetrazolyl)pyrazine-2-carboxamide in 15 ml of dimethylsulfoxide, 6.16 g of p-anisidine was added, and the mixture was heated for 18 hours 80°–90 ° C. Water and 10%-sodium hydroxide aqueous solution was added to the reaction mixture, and the aqueous alkaline solution was washed with chloroform. Aqueous layer was filtered, and the filtrate was adjusted with 10%-hydrochloric acid to pH 3. The precipitate was collected by filtration, and recrystalized from a mixture of dimethylsulfoxide and methanol affording 1.02 g of the desired compound as reddish yellow crystals, m.p. 291°–294 ° C. (decomp.).

Analysis: $C_{13}H_{12}N_8O_2$: Calcd. %: C,50.00; H,3.87; N,35.88. Found %: C,50.08; H,4.05; N,36.05.

The compounds described in Example 22–34 were prepared in the same manner as that described in Example 1–21. The physical properties of the compounds described in Examples 22-34 were shown in Tables 3-4.

TABLE 3

$$R_1R_2N\text{-pyrazine-}CONH\text{-tetrazole}$$

| Example No. | R₁ | R₂ | Salt or free base | Crystals | Melting point | Solvent | Formula | Elementary analysis (upper: Calcd. % / lower: Found %) |
|---|---|---|---|---|---|---|---|---|
| 22 | H | n-butyl | free base | pale yellow needles | 269~272°(decomp.) | DMF—EtOH | $C_{10}H_{14}N_8O$ | C, 45.80; H, 5.38; N, 42.72 / C, 45.65; H, 5.53; N, 42.83 |
| 23 | H | isobutyl | free base | pale yellow prisms | 265~275°(decomp.) | DMSO—EtOH | $C_{10}H_{14}N_8O$ | C, 45.80; H, 5.38; N, 42.72 / C, 45.77; H, 5.38; N, 42.82 |
| 24 | H | sec-butyl | free base | pale yellow needles | 265~269°(decomp.) | DMF—EtOH | $C_{10}H_{14}N_8O$ | C, 45.80; H, 5.38; N, 42.72 / C, 45.54; H, 5.36; N, 42.49 |
| 25 | H | tert-butyl | free base | yellow crystals | 266~270°(decomp.) | DMF—EtOH | | |
| 26 | H | n-hexyl | free base | colorless needles | 263~267°(decomp.) | DMF—EtOH | $C_{12}H_{18}N_8O$ | C, 49.64; H, 6.25; N, 38.60 / C, 49.54; H, 6.26; N, 38.48 |
| 27 | H | n-dodecyl | free base | colorless needles | 250~259°(decomp.) | DMSO—EtOH | $C_{18}H_{30}N_8O$ | C, 57.73; H, 8.07; N, 29.92 / C, 57.85; H, 8.09; N, 29.92 |
| 28 | H | cyclopropyl | free base | pale yellow crystals | 272~280°(decomp.) | DMSO—EtOH | $C_9H_{10}N_8O$ | C, 43.90; H, 4.09; N, 45.51 / C, 44.01; H, 4.20; N, 45.70 |
| 29 | H | cyclohexyl | free base | pale yellow needles | 287~291°(decomp.) | DMSO—EtOH | $C_{12}H_{16}N_8O$ | C, 49.99; H, 5.59; N, 38.87 / C, 49.99; H, 5.76; N, 38.88 |

TABLE 4

| Example No. | $R_1R_2N-$ | Salt or free base | Crystals | Melting point | Solvent | Formula | Elementary analysis (upper: Calcd. % / lower: Found %) |
|---|---|---|---|---|---|---|---|
| 30 | piperazin-1-yl (HN-piperazine) | free base | pale yellow crystals | >300° | H₂O | $C_{10}H_{13}N_9O\cdot\tfrac{1}{2}H_2O$ | C, 42.25; H, 4.96; N, 44.34 / C, 41.90; H, 4.89; N, 44.23 |
| 31 | 4-ethylpiperazin-1-yl (Et-N-piperazine) | HCl salt | yellow crystals | 230~243°(decomp.) | DMSO—MeOH | $C_{12}H_{17}N_9O\cdot HCl$ | C, 42.42; H, 5.34; N, 37.10 / C, 42.59; H, 5.55; N, 36.83 |
| 32 | 4-phenylpiperazin-1-yl | free base | yellow needles | 250~262°(decomp.) | DMF—EtOH | $C_{16}H_{17}N_9O$ | C, 54.69; H, 4.84; N, 35.88 / C, 54.66; H, 4.92; N, 36.02 |
| 33 | homopiperazin-1-yl (HN-homopiperazine) | free base | pale yellow crystals | 295~300°(decomp.) | H₂O | $C_{11}H_{15}N_9O$ | C, 45.67; H, 5.23; N, 43.57 / C, 45.37; H, 5.42; N, 43.42 |
| 34 | 4-methylhomopiperazin-1-yl (Me-N-homopiperazine) | free base | pale yellow crystals | >300° | H₂O | $C_{12}H_{17}N_9O$ | C, 47.52; H, 5.65; N, 41.50 / C, 47.71; H, 5.66; N, 41.32 |

We claim:

1. A pyrazine compound represented by the formula

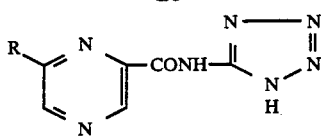

wherein R represents hydrogen or

wherein $R_1$ and $R_2$ may be the same or different and each independently represents hydrogen, straight or branched-chain lower -alkyl, or cycloalkyl having three to six carbon atoms inclusive, phenyl which may be substituted with halogen, lower-alkyl, or lower-alkoxy, or wherein $R_1$ and $R_2$ together represent alkylene of four to six carbon atoms, inclsuive, optionally interrupted by one or two nitrogen atoms or one oxygen atoms and said ring being optionally substituted by straight or branched-chain lower-alkyl having one to six carbon atoms inclusive, hydroxy, or phenyl, and pharmaceutically-acceptable salts thereof.

2. Compound of claim 1 being 6-(methylamino)-N-(1H-5-tetrazolyl)pyrazine-2-carboxamide.

3. Compound of claim 1 being 6-(ethylamino)-N-(1H-5-tetrazolyl)pyrazine-2-carboxamide.

4. Compound of claim 1 being (isopropylamino)-N-(1H-5-tetrazolyl)pyrazine- 2-carboxamide.

5. Compound of claim 1 being 6-(dimethylamino)-N-(1H-5-tetrazolyl)pyrazine-2-carboxamide.

6. Compound of claim 1 being 6-(pyrrolidinhyl)-N-(1H-5-tetrazolyl)pyrazine-2-carboxamide.

7. Compound of claim 1 being 6-(pyrrolidinyl)-N-(1H-5-tetrazolyl)pyrazine-2-carboxamide sodium salt.

8. Compound of claim 1 being 6-(4-methyl-1-piperazinyl)-N-(1H-5-tetrazolyl)pyrazine-2-carboxamide. hydrochloride.

9. Compound of claim 1 being 6-(phyenylamino)N-(1H-5-tetrazolyl)pyrazine-2-carboxamide compounds.

10. pharmaceutical composition useful in the treatment of allergen-induced hypersensitivity reactions mediated by release of histamine, comprising one or more compounds as claimed in claim 1, in an amount effective to inhibit histamine release, together with a pharmaceutically-acceptable carrier or coating.

11. A method for the treatment of a subject afflicted with an allergen-induced hypersensitivity reaction mediated by release of histamine, comprising the step of administering to the said subect an amount of a compound of claim 1 which is effective to inhibit histamine release.

* * * * *

UNITED STATES PATENT AND TRADEMARK OFFICE
CERTIFICATE OF CORRECTION

PATENT NO. : 4,792,547
DATED : December 20, 1988
Page 1 of 3
INVENTOR(S) : Yasuo Itoh, Hideo Kato, Eiichi Koshinaka, Nobuo Ogawa and
Kazuya Mitani It is certified that error appears in the above-identified patent and that said Letters Patent is hereby corrected as shown below:

Title Page, [56] References Cited, FOREIGN PATENT DOCUMENTS; "005979" should read -- 62-005979 --
Title Page, [57] ABSTRACT, line 2; "gastorenteric" should read -- gastroenteric --
Title Page, [57] ABSTRACT, line 3; "allertic" should read -- allergic --

Col. 1, line 6; "yyrazine" should read -- pyrazine --
Col. 1, line 10; delete "of" (first occurrence)
Col. 1, line 34; delete "have" (second occurrence)
Col. 1, line 61; delete "as"
Col. 1, line 64; delete "of" (first occurrence)
Col. 2, line 5; "accompained" should read -- accompanied --

Col. 2, line 42; "pharamaceutically-" should read -- pharmaceutically- --
Col. 2, line 49; "ar" should read -- are --
Col. 2, line 53; "propyl-" should read -- propyl-, --
Col. 2, line 54; delete "," (first occurrence in line)
Col. 2, line 56; "7membered-" should read -- 7 membered- --
Col. 2, line 62; "4-methylhomopiperazinylgroup" should read -- 4-methylhomopiperazinyl group --
Col. 3, line 31; "buaanol;" should read -- butanol; --
Col. 3, line 39; "dimethysufoxide." should read -- dimethylsulfoxide. --
Col. 3, line 42; "prefeable" should read -- preferably --

Col. 4, line 10; "anhyrride," should read -- anhydride, --
Col. 4, line 43; "an" should read -- and --
Col. 4, line 55; "Okmura," should read -- Okumura, --
Col. 4, line 65; "2 min." should read -- 20 min. --
Col. 4, line 65; "reactio" should read -- reaction --
Col. 6, line 1; "aleviate" should read -- alleviate --
Col. 6, line 10; "dyes" should read -- eyes --
Col. 6, line 11; "mg" should read -- mg, --
Col. 6, line 24; after "way" insert -- of --

UNITED STATES PATENT AND TRADEMARK OFFICE
CERTIFICATE OF CORRECTION

PATENT NO. : 4,792,547

DATED : December 20, 1988

INVENTOR(S) : Yasuo Itoh, Hideo Kato, Eiichi Koshinaka, Nobuo Ogawa and Kazuya Mitani It is certified that error appears in the above-identified patent and that said Letters Patent is hereby corrected as shown below:

Col. 6, line 41; "-26° C." should read -- -264° C. --
Col. 7, line 32; "6-choloro-" should read -- 6-chloro- --
Col. 8, line 32; "solutron" should read -- solution --
Col. 8, line 63; "hours," should read -- hours. --
Col. 9, line 6; "Ml" should read -- ml --
Col. 9, line 28; "fo" should read -- of --
Col. 9, line 50; "reation" should read -- reaction --
Col. 11, line 8; "2.26" should read -- 2.26 g --
Col. 11, line 17; "C,38.22;" should read -- C,38.62; --
Col. 11, line 40; "-Cholorophenyl)amino]-" should read
 -- -Chlorophenyl)amino]- --
Col. 12, line 12; "-tetrzo-" should read -- -tetrazo- --
Col. 12, line 25; "H,43.08;" should read -- H,4.08; --
Col. 12, line 48; "-tetrazoly)" should read -- -tetrazolyl) --
Col. 13, line 1; "were" should read -- are --
Col. 15, line 21; "inclsuive," should read -- inclusive, --

Col. 15, line 23; "atoms" should read -- atom --

Col. 16, line 7; "6-(pyrrolidinhyl)-" should read --6-(pyrrolidinyl)- --
Col. 16, line 13; delete the period "." after "mide"
Col. 16, line 14; "6-(phyenylamino)" should read -- 6-(phenylamino) --
Col. 16, line 15; delete "compounds"

UNITED STATES PATENT AND TRADEMARK OFFICE
CERTIFICATE OF CORRECTION

PATENT NO. : 4,792,547

DATED : December 20, 1988

INVENTOR(S) : Yasuo Itoh, Hideo Kato, Eiichi Koshinaka, Nobuo Ogawa and Kazuya Mitani It is certified that error appears in the above-identified patent and that said Letters Patent is hereby corrected as shown below:

Col. 16, line 16; "pharmaceutical" should read -- Pharmaceutical --

Col. 16, line 25; "subect" should read -- subject --

Signed and Sealed this

Twenty-first Day of November, 1989

*Attest:*

JEFFREY M. SAMUELS

*Attesting Officer*    *Acting Commissioner of Patents and Trademarks*